United States Patent
Kotwal et al.

(10) Patent No.: US 7,897,561 B2
(45) Date of Patent: *Mar. 1, 2011

(54) METHODS FOR TREATMENT OR PROPHYLAXIS OF ATHEROSCLEROSIS AND REPERFUSION INJURY

(75) Inventors: Girish J. Kotwal, Louisville, KY (US); Gudmundur Johann Arason, Reykjavik (IS)

(73) Assignees: Girish J. Kotwal, Louisville, KY (US); Gudmundur J. Arason, Reykjavik (IS)

( * ) Notice: Subject to any disclaimer, the term of this patent is extended or adjusted under 35 U.S.C. 154(b) by 172 days.

This patent is subject to a terminal disclaimer.

(21) Appl. No.: 11/916,760

(22) PCT Filed: Jun. 5, 2006

(86) PCT No.: PCT/IB2006/051784
§ 371 (c)(1),
(2), (4) Date: Dec. 6, 2007

(87) PCT Pub. No.: WO2006/131874
PCT Pub. Date: Dec. 14, 2006

(65) Prior Publication Data
US 2008/0200645 A1    Aug. 21, 2008

Related U.S. Application Data

(60) Provisional application No. 60/687,766, filed on Jun. 6, 2005.

(51) Int. Cl.
*A61K 38/16*    (2006.01)

(52) U.S. Cl. .................................... 514/2; 514/12
(58) Field of Classification Search .................. None
See application file for complete search history.

(56) References Cited

U.S. PATENT DOCUMENTS

| 5,157,110 A | 10/1992 | Kotwal et al. |
| 5,187,268 A | 2/1993 | Kotwal et al. |
| 5,942,405 A * | 8/1999 | Ames et al. .................. 435/7.24 |
| 6,193,979 B1 * | 2/2001 | Rittershaus et al. ..... 424/195.11 |
| 2003/0096775 A1 | 5/2003 | Graham et al. |
| 2008/0267980 A1 * | 10/2008 | Tomlinson et al. ........ 424/178.1 |

FOREIGN PATENT DOCUMENTS

WO    9400571    1/1994

(Continued)

OTHER PUBLICATIONS

Niculescu et al. The Role of Complement Activation in Atherosclerosis. Immunologic Research. 2004, vol. 30, No. 1, pp. 73-80.*

(Continued)

*Primary Examiner* — Jeffrey E Russel
(74) *Attorney, Agent, or Firm* — Stites & Harbison, PLLC; Terry L. Wright

(57) ABSTRACT

The invention includes a method for the treatment or prophylaxis of atherosclerosis, and/or for the treatment or prophylaxis of reperfusion injury in a subject in need of treatment by administering to the subject a therapeutically effective amount of a complement inhibitor. The complement inhibitor may be a molecule which can inhibit activation of at least one complement component, inhibit activity of at least one activated complement component, act as an antagonist against at least one complement receptor, or combinations thereof. The complement inhibitor can be a vaccinia virus complement control protein (VCP).

17 Claims, 10 Drawing Sheets

FOREIGN PATENT DOCUMENTS

| WO | 9747321 | | 12/1997 |
|---|---|---|---|
| WO | WO 00/43027 | A1 * | 7/2000 |
| WO | 0112212 | | 2/2001 |
| WO | 03097104 | | 11/2003 |
| WO | 2004007553 | | 1/2004 |
| WO | 2004043925 | | 5/2004 |
| WO | 2006136982 | | 12/2006 |

OTHER PUBLICATIONS

Amsterdam et al., "Limitation of reperfusion injury by a monoclonal antibody to C5a during myocardial infarction in pigs," Am J Physiol., vol. 268, , 1995, pp. H448-H457.

Anderson t al., "Vaccinia Virus Complement Control Protein Ameliorates Hyperacute Xenorejection by Inhibiting Xenoantibody Binding," Transplantation Proceedings, vol. 34, No. 8, 2002, pp. 3277-3281.

Baker et al., "Studies on the Inhibition of C56-Induced Lysis (Reactive Lysis)—VI. Modulation of C56-Induced Lysis by Polyanions and Polycations," J. Immunol., vol. 114, 1975, pp. 554-558.

Buerke et al., "Novel Small Molecule Inhibitor of C1s Exerts Cardioprotective Effects in Ischemia-Referfusion Injury in Rabbits," J Immunol, vol. 167, 2001, pp. 5375-5380.

De Zwaan, et al., "Continuous 48-h C1-inhibitor treatment, following reperfusion therapy, in patients with acute myocardial infarction," Eur Heart J., vol. 21, 2002, pp. 1670-1677.

Englberger et al., "Rosmarinic Acid: A New Inhibitor of Complement C-3-Convertase With Anti-Inflammatory Activity," Int. J. Immunopharmacol., vol. 10, 1988, pp. 729-737.

Fujii et al., "New Synthetic Inhibitors of C1F, C1 Esterase, Thrombin, Plasmin, Kallikrein and Trypsin," Biochim. Biophys. Acta, vol. 661, 1981, pp. 342-345.

Granger et al., "Pexelizumab, an Anti-C5 Complement Antibody, as Adjunctive Therapy to Primary Percutaneous Coronary Intervention in Acute Myocardial Infarction: The COMplement inhibition in Myocardial infarction treated with Angioplasty (COMMA) Trial," Circulation, vol. 108, 2003, pp. 1184-1190.

Hong et al., "Inhibitory Effect of K-76 Monocarboxylic Acid, an Anticomplementary Agent, on the C3b Inactivator System," J. Immunol., vol. 127, 1981, pp. 104-108.

Horstick et al., "Application of C1-Esterase Inhibitor During Reperfusion of Ischemic Myocardium: Dose-Related Beneficial Versus Detrimental Effects," Circulation, vol. 104, 2001, pp. 3125-3131.

Inagi et al., "FUT-175 as a potent inhibitor of C5/C3 convertase activity for production of C5a and C3a," Immunol. Lett., vol. 27, 1991, pp. 49-52.

Kotwal et al., "Vaccinia virus encodes a secretory polypeptide structurally related to complement control proteins," Nature, vol. 335 (6186), 1988, pp. 176-178.

Kotwal et al., "Vaccinia Virus Encodes Two Proteins That Are Structurally Related to Members of the Plasma Serine Protease Inhibitor Superfamily," J. Virol., vol. 63, 1989, pp. 600-606.

Kotwal et al., "Inhibition of the Complement Cascade by the Major Secretory Protein of Vaccinia Virus," Science, vol. 250 (4982), 1990, pp. 827-830.

Kroshus et al., "Complement Inhibition With An Anti-C5 Monoclonal Antibody Prevents Acute Cardiac Tissue Injury In An Ex Vivo Model Of Pigs-to-Human Xenotransplantation," Transplantation, vol. 60, 1995, pp. 1194-1202).

Lazar et al., "Soluble Complement Receptor Type I Limits Damage During Revascularization of Ischemic Myocardium," Ann Thorac Surg., vol. 65, 1998, pp. 973-977).

Lazar et al., "Total Complement Inhibition: An Effective Stratgey to Limit Ischemic Injury During Coronary Revascularization on Cardiopulmonary Bypass," Circulation, vol. 100, 1999, pp. 1438-1442.

Mahaffey et al., "Effect of Pexelizumab, an Anti-C5 Complement Antibody, as Adjunctive Therapy to Fibrinolysis in Acute Myocardial Infarction: The COMplement Inhibition in myocardial infarction treated with thromboLYtics (COMPLY) Trial," Comply; vol. 108, 2003, pp. 1176-1183.

Mckenzie et al., "Regulation of Complement Activity by Vaccinia Virus Complement-Control Protein," J. Infect. Dis., vol. 166, 1992, pp. 1245-1250.

Morgan et al., "Complement therapeutics; history and current progress," Mol. Immunol., vol. 40, 2003, pp. 159-170.

Murthy et al., "Crystal Structure of a Complement Control Protein that Regulates Both Pathways of Complement Activiation and Binds Heparan Sulfate Proteoglycans," Cell, vol. 104, 2001, pp. 301-311.

Park et al., "N-Acetylheparin Pretreatment Reduces Infarct Size in the Rabbit," Pharmacology; vol. 58, 1999, pp. 120-131.

Reynolds et al., "Vaccinia Virus Complement Control Protein Reduces Inflammation and Improves Spinal Cord Integrity Following Spinal Cord Injury," Ann. NY Acad. Sci., vol. 1035, 2004, pp. 165-178.

Riley et al., "Recombinant Human Complement C5A Receptor Antagonist Reduces Infarct Size After Surgical Revascularization," J Thorac Cardiovasc Surg; vol. 120, 2000, pp. 350-358.

Sahu et al., "Inhibition of Human Complement by a C3-Binding Peptide Isolated from a Phage-Displayed Random Peptide Library," J. Immunol., vol. 157, 1996, pp. 884-891.

Sahu et al., "Interaction of Vaccinia Virus Complement Control Protein with Human Complement Proteins: Factor I-Mediated Degradation of C3b to iC3b1, Inactivates the Alternative Complement Pathway," J. Immunol., vol. 160, 1998, pp. 5596-5604.

Sahu et al., "Inhibition of Complement by Covalent Attachment of Rosmarinic Acid to Activated C3b," Biochem. Pharmacol. vol. 57, 1999, pp. 1439-1446.

Smith et al., "Reduction of myocardial reperfusion injury with human soluble complement receptor type 1 (BRL 55730)," Eur J Pharmacol; vol. 236, 1993, pp. 477-481.

Smith et al., "Conserved Surface-Exposed K/R-X-K/R Motifs and Net Positive Charge on Poxvirus Complement Control Proteins Serve as Putative Heparin Binding sites and Contribute to Inhibition of Molecular Interactions with Human Endothelial Cells: a Novel Mechanism for Evasion of Host Defense," J. Virol., vol. 74, 2000, pp. 5659-5666.

Smith et al., "Mapping of regions within the vaccinia virus complement control protein involved in dose-dependent binding to key complement components and heparin using surface plasmon resonance," Biochim, Biophys. Acta, vol. 1650, 2003, pp. 30-39.

Tanhehco et al., "Reduction of Myocardial Infarct Size After Ischemia and Reperfusion by the Glycosaminoglycan Pentosan Polysulfate," J Cardiovasc Pharmacol., vol. 34, 1999, pp. 153-161.

Thorbjornsdottir et al., "Vaccinia Virus Complement Control Protein Diminishes Formation of Atherosclerotic Lesions," Ann N Y Acad Sci,. vol. 1056, 2005, pp. 1-15.

Vakeva et al., "Myocardial Infarction and Apoptosis After Myocardial Ischemia and Reperfusion: Role of the Terminal Complement Components and Inhibition by Anti-C5 Therapy," Circulation, vol. 97, 1998, pp. 2259-2267.

Verrier et al., "Terminal Complement Blockade With Pexelizumab During Coronary Artery Bypass Graft Surgery Requiring Cardiopulmonary Bypass," Jama., vol. 291, 2004, pp. 2319-2327.

Walport M.J., "Complement," N. Eng. J. Med., vol. 344, 2001, pp. 1058-1066 and pp. 1140-1144.

Weisman et al., "Soluble Human Complement Receptor Type 1: In Vivo Inhibitor Of Complement Suppressing Post-Ischemic Myocardial Inflammation and Necrosis," Science vol. 249(4965), 1990, pp. 146-151.

Weisman et al., "Recombinant Soluble CR1 Suppressed Complement Activation, Inflammation, and Necrosis Associated with Reperfusion of Ischemic Myocardium," Trans. Assoc. Am. Phys., vol. 103, 1990, pp. 64-72.

Zacharowski et al., "Reduction of myocardial infarct size with sCR1sLex, an alternatively glycosylated form of human soluble complement receptor type 1 (sCR1), possessing sialyl Lewis x," Br J Pharmacol, vol. 128, 1999, pp. 945-952.

Armstrong et al., "Concerning the mechanism of pexelizumab's benefit in acute myocardial infarction," Amer Heart Journal, vol. 151 (4), 2006, pp. 787-790.

Fattouch et al., "Beneficial effects of C1 esterase inhibitor in St-elevation myocardial infarction in patients who underwent surgical reperfusion: a randomised double-blind study," European Journal of Cardio-thoracic Surgery, 32, 2007, pp. 326-332.

Mullick et al., "Identification of Complement Regulatory Domains in Vaccinia Virus Complement Control Protein," J. Virol., vol. 79(19), 2005, pp. 12382-12393.

Ueda et al., "Inhibitory effects of newly synthesized active center-directed trypsin-like serine protease inhibitors on the complement system," Inflamm. Res., 49, 2000, pp. 42-46.

Vogel et al., "Humanized Cobra Venom Factor: Experimental Therapeutics for Targeted Complement Activation and Complement Depletion," Current Pharmaceutical Design, 13, 2007, pp. 2916-2926.

Mitsui et al., "Effect of Anticomplement Agent K-76 on Experimental Atherosclerosis in Rabbits," Journal of Nihon University Medical Association, vol. 49, No. 4, 1990, pp. 357-365.

ISA/Eurpean Patent Office, International Search Report and Written Opinion for international application No. PCT/IB2006/051784, completed Nov. 7, 2006.

* cited by examiner

METHODS FOR TREATMENT OR PROPHYLAXIS OF ATHEROSCLEROSIS AND REPERFUSION INJURY

BACKGROUND

Atherosclerosis is the leading cause of death in all regions of the world except sub-Saharan Africa, with prevalence values of 85% at age 50 and an overall global mortality rate of >40%. It is a slow process, beginning as a benign accumulation of low-density lipoproteins (LDL) in the intima of large and medium-sized arteries in the first decade of life, leading to clinical problems primarily in the middle-aged and elderly through further development of early lesions (fatty streaks) to fibrotic plaques and complicated lesions. The most severe clinical condition is associated with lesion rupture, causing infarction of an artery supplying the heart (myocardial infarction, MI), the brain (stroke) or peripheral tissues (peripheral artery disease, PAD). Injury to cardiac tissue can also result from the removal of occlusions and reperfusion of the tissue, causing further morbidity and mortality. Therefore, there is an ongoing need for novel therapeutics for the treatment and prophylaxis of atherosclerosis and reperfusion injury.

SUMMARY

The presently disclosed subject matter provides, in some embodiments, methods for the treatment or prophylaxis of atherosclerosis in a subject in need thereof. In some embodiments, the methods comprise administering to the subject a therapeutically effective amount of a complement inhibitor.

In other embodiments, the presently disclosed subject matter provides methods of inhibiting the production or progression of one or more atherosclerotic lesions within the vasculature of a subject. The methods comprise administering to the subject a therapeutically effective amount of a complement inhibitor.

In still further embodiments, the presently disclosed subject matter provides methods of treatment or prophylaxis for a reperfusion injury in a subject in need of treatment. In some embodiments, the methods comprise administering to the subject a therapeutically effective amount of a vaccinia complement control (VCP) polypeptide or a biologically active derivative or fragment thereof having complement inhibitor activity.

DETAILED DESCRIPTION

As used herein, "atherosclerosis" refers to a disorder characterized by the deposition of plaques containing cholesterol and lipids on the innermost layer of the walls of large and medium-sized arteries. Atherosclerosis can also be characterized as a chronic inflammatory disease in which the presence of LDL particles in the vascular wall leads to recruitment of monocytes from the blood, their transformation into macrophages and a dynamic but ultimately unsuccessful attempt to eliminate the LDL particles by phagocytosis. Both the innate and the adaptive immune system appear to contribute to the development of the lesions, and as in many other inflammatory diseases, activation of complement appears to mediate at least part of the tissue damage.

Complement forms an important part of the innate immune system. It comprises about 30 proteins, some of which act within a cascade-like reaction sequence, while others serve as control proteins or as cellular receptors. For a review of the complement system, see Walport, M. J. (2001), N. Eng. J. Med., vol. 344, pp. 1058-1066 and Walport, M. J. (2001), N. Eng. J. Med., vol. 344, pp. 1140-1144, herein incorporated by reference. Certain components are present in the blood in precursor forms and must be activated. Complement can be activated by any of three pathways, (1) the antibody-dependent classical pathway (C1-C4-C2-C3), (2) the carbohydrate-dependent lectin pathway (MBL-C4-C2-C3), and (3) the alternative pathway (C3b-Factor B-C3), which is triggered directly by pathogen surfaces. Activated complement has many functions, including initiation of inflammation, recruitment of leukocytes, clearance of immune complexes, neutralization of pathogens, regulation of antibody responses and cytolysis (the lytic pathway, via C5b-C6-C7-C8-C9, i.e. the membrane attack complex (MAC)). The complement system is a very powerful mediator of inflammation, and complement activation generates proinflammatory peptides such as the anaphylatoxins C3a and C5a, which recruit and activate leukocytes, the cell-bound opsonins C4b and C3b, which facilitate phagocytosis of the target, and MAC, i.e. C5b-9, which lyses target cells and may activate bystander cells to release pro-inflammatory mediators. Uncontrolled activation of complement and consequent host cell damage is prevented by a vast array of regulatory proteins, either circulating in plasma or expressed at the cell surface.

Considerable clinical and experimental evidence implicates complement in the pathogenesis of atherosclerosis. Immunoglobulins, C3, C4, complement regulators and terminal complexes C5b-9 have all been immunolocalized in human atherosclerotic plaques, suggesting local activation of complement. Animal studies indicate that complement activation forms a link between LDL deposition and monocyte recruitment. Deficiency in complement C6 has been shown to protect against diet-induced atherosclerosis in rabbits. Two independent lines of evidence suggest a central involvement of C4 in disease pathology. These results suggest that complement has a role in the development of lesions and are consistent with the notion that chronic activation of complement by modified LDL leads to monocyte recruitment, foam cell formation and lesion progression. In contrast, studies on mice with a combined deficiency in complement (C3 or C5) and a key element in lipid metabolism (LDL-R, ApoE or both) reported that the development of atherosclerotic lesions was not severely affected. This may reflect a difference between diet-induced and genetically driven disease.

The tendency to develop atherosclerosis differs between animal species as well as strains. The C57BL/6 strain is very susceptible to develop diet-induced atherosclerosis; furthermore, lesions are restricted to the fatty streak stage. Genetically modified mouse strains (ApoE-/-, LDLR-/-) that can form more extensive lesions are also available. They are particularly useful in experiments requiring more accelerated disease and/or progression of lesions beyond the fatty streak stage. These mice do show lesions more similar to the human atherosclerotic lesions, but in human, the course of the disease is quite different as it is diet induced and usually not because of genetic defects in major lipid transport proteins. The suitability of ApoE-/- and LDLR-/- mice for revealing the atherogenic effect of complement has recently been questioned; the atherogenic drive of these mice is much stronger than that of the human and it is difficult to predict the effect of combined life-long deficiency of complement as well as key components in lipid transport. In order to test whether the discrepancies in previous animal studies are due to differences between species or between genetically driven and diet-induced disease, we used wild-type mice of the C57BL strain, the background strain of ApoE-/- and LDLR-/- mice, and tested the importance of complement by using an inhibitor instead of gene knock-out.

Complement inhibitors have not been previously used in models of atherosclerotic development. Complement inhibitors have however been used in reperfusion injury with very promising results and therapy with complement inhibitors is approaching the clinic.

Studies on complement inhibitors in animal models of myocardial infarction has provided convincing evidence of participation of complement in reperfusion injury. Previous experimental studies on animals have shown that inhibition of complement activation, either at the time of coronary artery occlusion or just before reperfusion reduces infarct size and neutrophil infiltration. Therefore, inhibiting complement activation in order to reduce ischemic/reperfusion injury has been regarded promising.

The first evidence that complement activation had deleterious effect on tissue integrity during ischemia/reperfusion was presented in 1978. It was shown that by depleting complement with cobra venom factor (CVF), the infarct size in an animal model was significantly reduced. This drove researchers to develop more suitable inhibitors to prevent complement activation, as CVF is not a good inhibitor in animals and humans because it leads to biologically active complement products. Today complement inhibitors have been developed which have specific actions on the complement cascade and are poorly immunogenic. Various recombinant human complement inhibitors have been developed, as well as monoclonal antibodies, synthetic peptides and peptidomimetics which block activation of certain complement components, neutralize an activation fragment or antagonize complement receptors.

Modern studies on the involvement of complement in reperfusion injury are based on the use of genetically deficient animal strains, such as C6 deficient rabbits in which ischemia/reperfusion injury was reduced compared to complement sufficient controls, or the use of complement inhibitors in wild type strains. The inhibitors; soluble CR1 (sCR1), C1 esterase inhibitor (C1-INH), C5a monoclonal antibody and C5a receptor antagonist have all been shown to reduce ischemic/reperfusion injury by reducing infiltration of neutrophils and reducing the inflammatory response. Despite promising results in experimental models, clinical trials in humans have not been as promising. The use of sCR1 in man was trialed in patients during cardiopulmonary bypass, the agent proved safe but there were no clinically important differences between the patients who received sCR1 and those receiving the placebo. Further development of this agent was terminated. C1-INH initially showed promising results in clinical trials, but a study involving its application to reduce capillary leak during open-heart surgery in 13 neonates lead to nine deaths due to venous thrombosis. It has now been shown that C1-INH has cardioprotective effect at low doses (20-40 IU/kg), but at higher doses the detrimental effects come to light. Human studies using the novel C5 monoclonal antibody, pexelizumab, either in thrombolytic therapy or angioplasty after MI showed no significant effect of the C5 antibody in reduction of tissue damage. However in the latter study the 90 day mortality was somewhat reduced in those receiving the antibody. In addition a large clinical study on patients undergoing cardiopulmonary bypass receiving pexelizumab showed no statistically significant difference on the primary endpoint between those receiving the drug and those receiving placebo, but reduction in mortalities or subsequent MI was found.

In some embodiments, the methods of the presently disclosed subject matter are useful for treating atherosclerosis by administering a complement inhibitor in that they inhibit the onset, growth, or spread of atherosclerotic lesions within the vasculature of a subject, cause regression of the atherosclerotic lesions, cure the atherosclerosis, or otherwise improve the general well-being of a subject afflicted with, or at risk of, contracting atherosclerosis. Thus, in accordance with the presently disclosed subject matter, the terms "treat", "treating", and grammatical variations thereof, as well as the phrase "method of treating", are meant to encompass any desired therapeutic intervention, including but not limited to a method for treating an existing atherosclerotic condition in a subject.

The presently disclosed subject matter further provides for the prophylactic administration of a complement inhibitor. That is, the complement inhibitor is administered prophylactically to retard the onset or even prevent atherosclerosis or to retard the onset or even prevent the recurrence of atherosclerosis. Thus, in some embodiments, a complement inhibitor is administered prophylactically to prevent or reduce the incidence of one of: (a) atherosclerosis in a subject at risk for atherosclerosis; (b) a recurrence of atherosclerosis; and (c) combinations thereof.

The presently disclosed subject matter still further provides for the administration of a vaccinia complement control (VCP) polypeptide or a biologically active derivative or fragment thereof having complement inhibitor activity for the treatment or prophylaxis of a reperfusion injury to a subject in need of such treatment. Reperfusion injury can occur in a subject after removal of a vascular occlusion. Blockage of vasculature causes areas of ischemia in tissue normally fed by the vasculature. Re-establishing blood flow to the ischemic tissue can result in damage to the tissue. Complement has been demonstrated to play a role in the reperfusion injury. For example, reperfusion of one or more coronary arteries after a myocardial infarction, such as by for example administration of a thrombolytic agent (e.g. tissue plasminogen activator (tPA)), can result in reperfusion injury. As such, the presently disclosed subject matter provides for the treatment or prophylaxis of a reperfusion injury through the administration of a complement inhibitor, such as for example VCP, which can prevent or reduce the activation and activity of complement at the site of reperfusion. As a majority of the reperfusion injury occurs shortly after the reperfusion event, in some embodiments, the VCP is administered shortly before or during reperfusion. In some embodiments, the VCP can be administered as a single bolus shortly before or during reperfusion.

Further with respect to the therapeutic methods of the presently disclosed subject matter, a preferred subject is a vertebrate subject. A preferred vertebrate is warm-blooded; a preferred warm-blooded vertebrate is a mammal. A preferred mammal is most preferably a human. As used herein, the term "subject" includes both human and animal subjects. Thus, veterinary therapeutic uses are provided in accordance with the presently disclosed subject matter.

As such, the presently disclosed subject matter provides for the treatment of mammals such as humans, as well as those mammals of importance due to being endangered, such as Siberian tigers; of economical importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economical importance to humans. Thus, also provided is the treatment of livestock, including, but not limited to, domesticated swine, ruminants, ungulates, horses (including race horses), poultry, and the like.

As used herein, the phrase "therapeutically effective amount" refers to an amount of a therapeutic composition sufficient to produce a measurable response (e.g., a biologically or clinically relevant response in a subject being treated) when administered to a subject. Actual dosage levels of active ingredients in the pharmaceutical compositions of the presently disclosed subject matter can be varied so as to administer an amount of the active compound(s) that is effective to achieve the desired therapeutic response for a particular subject. The selected dosage level will depend upon the activity of the therapeutic composition, the route of administration, combination with other drugs or treatments, the severity of the condition being treated, and the condition and prior medical history of the subject being treated. However, it is within the skill of the art to start doses of the compound at levels lower than required to achieve the desired therapeutic effect and to gradually increase the dosage until the desired effect is achieved.

The potency of a therapeutic composition can vary, and therefore a "therapeutically effective amount" can vary. However, one skilled in the art can readily assess the potency and efficacy of a candidate compound of the presently disclosed subject matter and adjust the therapeutic regimen accordingly. In some embodiments, for example, a therapeutically effective amount of a complement inhibitor for the treatment and/or prophylaxis of atherosclerosis is from about 0.01 g/kg to about 0.1 g/kg per dose.

In some embodiments, the compound is administered orally or parenterally in dosage unit formulations containing standard, well-known nontoxic physiologically acceptable carriers, adjuvants, and vehicles as desired. The term "parenteral" as used herein includes intravenous, intracerebroventricular, intramuscular, intra-arterial injection, and infusion techniques.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic parenterally acceptable diluent or solvent. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

Preferred carriers include neutral saline solutions buffered with phosphate, lactate, Tris, and the like. Of course, one of skill would know to purify the carrier and therapeutic compound sufficiently to render it essentially free of undesirable contaminants, such as endotoxins and other pyrogens such that it does not cause any untoward reactions in the subject receiving the formulation.

The presently disclosed subject matter provides in some embodiments for the administration of complement inhibitors for the treatment and prophylaxis of atherosclerosis and for the inhibition of the production or progression of atherosclerotic lesions in a subject. A "complement inhibitor" is a molecule that can block activation or activity of one or more components of at least one of the complement pathways, thereby preventing or decreasing the effects of complement activation. In some embodiments of the presently disclosed subject matter, a complement inhibitor is a molecule which can inhibit activation of at least one complement component, inhibit activity of at least one activated complement component, act as an antagonist against at least one complement receptor, or combinations thereof. The complement inhibitor can be in some embodiments a natural, purified peptide, including antibodies, synthetic peptides, peptidomimetics, and natural or synthetic small molecules.

In some embodiments, the complement component inhibited by the complement inhibitor can be, for example, C1, C2, C3, C4, C5, C6, C7, C8, C9, Factor B, Factor D, Properdin, or combinations thereof. Further, in some embodiments, the activated complement component inhibited by the complement inhibitor can be, for example, C1r, C1s, C2a, C3a, C3b, C4a, C4b, C5a, C5b, Bb, C3 convertase, C5 convertase, MAC, or combinations thereof. The C3 convertase can be a classical pathway C3 convertase or lectin pathway convertase, i.e. C4bC2a or an alternative pathway C3 convertase (C3bBb) and the C5 convertase can be a classical pathway C5 convertase (C4bC2aC3b) or an alternative pathway C5 convertase (C3bBbC3b). Still further, in some embodiments the complement receptor to which the complement inhibitor is an antagonist can be, for example, complement receptor 1 (CR1), CR2, CR3, CR4, or combinations thereof.

Complement inhibitors of numerous types are known in the art. See generally, Morgan, B. P. & Harris, C. L. (2003) *Mol. Immunol.*, vol. 40, pp. 159-170, incorporated herein by reference. Exemplary complement inhibitors include, but are not limited to: cobra venom factor, which is known to bind Factor B and thereby consume available C3 without activation of C3; polyanionic glycosaminoglycans, such as heparin, which binds and inactivates C1, blocks C3 convertase formation and MAC formation (see, for example, Baker, P. J. et al. (1975) *J. Immunol.*, vol. 114, pp. 554-558); small molecules, such as K76COOH, isolated from the fungus *Stachybotrys complementi*, which has been shown to inhibit complement activation at C5 (Hong. K. et al. (1981) *J. Immunol.*, vol. 127, pp. 104-108), Rosmarinic acid, initially isolated from the common Rosemary herb, which has been shown to bind C3b in the forming convertase (Engiberger, W. et al. (1988) *Int J. Immunopharmacol*, vol. 10, pp. 729-737 and Sahu, A. et al. (1999) *Biochem. Pharmacol.* Vol. 57, pp. 1439-1446.), and Nafamastat mesilate (FUT-175), a synthetic molecule shown to inhibit C1r, C1s, Factor D, and both C3 and C5 convertases (Fujii, S. & Hitomi, Y. (1981) *Biochim. Biophys. Acta*, vol. 661, pp. 342-345 and Inagi, R. et al. (1991) *Immunol. Lett.* Vol. 27, pp. 49-52.); peptide inhibitors of complements, such as for example, compstatin, which has been shown to bind C3 and prevent cleavage thereof (Sahu. A. et al. (1996) *J. Immunol.*, vol. 157, pp. 884-891); antibody inhibitors of complement activation that have binding specificity for different complement components, such as for example, the humanized anti-C5 monoclonal antibody h5G1.1 (Kroshus, T. J. et al. (1995) *Transplantation*, vol. 60, pp. 1194-1202); and soluble forms of complement regulators (CReg), which interact with C3 and C5 convertases, such as for example MCP, DAF, CR1, Factor H and C4bp, e.g., sCR1 has been shown to inhibit C3 and C5 convertase formation, prevent C3b opsonization, C5a generation, and MAC formation (Weisman, H. F., et al. (1990) *Trans. Assoc. Am. Phys.*, vol. 103, pp. 64-72 and Weisman, H. F. et al. (1990) *Science*, vol. 249, pp. 146-151).

In some preferred embodiments the complement inhibitor is a molecule having binding specificity for C3, C4, activated complement components thereof, or combinations thereof. Further, in some embodiments, the complement inhibitor inhibits formation of an active C3 convertase, promotes inactivation of the active C3 convertase, inhibits the conversion of C3 to C3b, or combinations thereof.

In particularly preferred embodiments, the complement inhibitor is a vaccinia complement control protein (VCP) or a biologically active derivative or fragment thereof having complement inhibitor activity. VCP is a strong inhibitor of the classical, lectin and alternative pathways of complement, acting on both C4 and C3. VCP is a 35 kDa, soluble, secreted product of the vaccinia virus containing four short consensus repeats that share the greatest sequence homology with several proteins of the regulators of complement activity (RCA) family, including C4 binding protein (C4-bp; 38% identity), membrane cofactor protein (MCP; 35% identity) and decay-accelerating factor (DAF; 31% identity). VCP shares the greatest functional similarity, however, with complement receptor 1 (CR1). VCP binds to C4b, blocks the formation of the classical pathway C3 convertase, binds C3b, causes the accelerated decay of the classical pathway convertase, and blocks the conversion of C3 to C3b in both the classical and alternative pathways by promoting Factor I cleavage of C3b. Like its soluble mammalian RCA counterparts C4-bp and Factor H, but unlike the membrane RCA molecules decay accelerating factor (DAF), membrane cofactor protein (MCP) and soluble complement receptor 1 (CR1), it displays heparin-binding capabilities, suggesting an in vivo role in connection with heparan sulfate proteoglycans lining the endothelial cell layer. By blocking complement activation at multiple sites, VCP downregulates proinflammatory chemotactic factors (C3a, C4a and C5a) resulting in reduced cellular influx and inflammation.

Further detailed description of VCP can be found in the following references, each of which is incorporated herein by reference: Kotwal, G. J. & Moss, B. (1988) *Nature*, vol. 335 (6186), pp. 176-178; Kotwal, G. J. & Moss, B. (1989) *J. Virol.*, vol. 63, pp. 690-696; U.S. Pat. No. 5,157,110; U.S. Pat. No. 5,187,268; Kotwal, G. J. et al. (1990) *Science*, vol. 250 (4982), pp. 827-830; McKenzie, R. et al. (1992) *J. Infect. Dis.*, vol. 166, pp. 1245-1250; Sahu, A. et al. (1998) *J. Immunol.*, vol. 160, pp. 5596-5604; Smith, S. A. et al. (2000) *J. Virol.*, vol. 74, pp. 5659-5666; Murthy, K. H. et al. (2001) *Cell*, vol. 104, pp. 301-311; and Smith, S. A. et al. (2003) *Biochim. Biophys. Acta*, vol. 1650, pp. 30-39. In view of the described functional characteristics of VCP, it is considered to be particularly well-suited for use in the methods of the presently disclosed subject matter.

In a further embodiment of the invention, there is provided the use of a complement inhibitor in the preparation of a medicament for the treatment or prophylaxis of atherosclerosis in a subject in need of treatment which includes administering to the subject a therapeutically effective amount of said medicament.

The invention extends further to the use of a complement inhibitor in the preparation of a medicament for inhibiting the production or progression of one or more atherosclerotic lesions within the vasculature of a subject, which includes administering to the subject a therapeutically effective amount of said medicament.

The subject may be a mammal, preferably a human.

Administering the complement inhibitor to the subject may comprise intravenously injecting the complement inhibitor into the subject. The therapeutically effective amount of the complement inhibitor will typically be between about 0.01 g/kg to about 0.1 g/kg per dose. The complement inhibitor may be a molecule which can inhibit activation of at least one complement component, inhibit activity of at least one activated complement component, act as an antagonist against at least one complement receptor, or combinations thereof.

The complement component may be selected from the group consisting of C1, C2, C3, C4, C5, C6, C7, C8, C9, Factor B, Factor D, Properdin, and combinations thereof. Preferably, it may be selected from the group consisting of C1r, C1s, C2a, C3a, C3b, C4a, C4b, C5a, C5b, Bb, C3bBb, C3 convertase, C5 convertase, membrane attack complex (MAC), and combinations thereof.

The C3 convertase may be a classical pathway C3 convertase or an alternative pathway C3 convertase and the C5 convertase may be a classical pathway C5 convertase or an alternative pathway C5 convertase. The complement receptor may be selected from the group consisting of CR1, CR2, CR3, CR4, and combinations thereof.

The complement inhibitor may be a molecule with binding specificity for C3, C4, activated complement components thereof, or combinations thereof. The complement inhibitor may inhibit formation of an active C3 convertase, promote inactivation of the active C3 convertase, inhibit the conversion of C3 to C3b, or combinations thereof. The C3 convertase may be a classical pathway C3 convertase or an alternative pathway C3 convertase.

The complement inhibitor may be a vaccinia virus complement control protein (VCP) or a biologically active derivative or fragment thereof having complement inhibitor activity.

The vasculature may comprise a cardiac artery. In particular, the vasculature may comprise an aorta. The method of the invention is naturally not limited to cardiac arteries and the aorta and the vascular lesions which can be treated or prevented can occur throughout the entire vascular tree.

The method of the invention is accordingly useful in treating or preventing lesions in, for example, the coronary arteries. Furthermore, since a stroke or a peripheral arterial disease is a remote effect or result of atherosclerosis the method of the invention is also useful in the treatment or prevention of strokes and peripheral arterial disease.

The invention extends, further, to the use of a vaccinia complement control (VCP) polypeptide or a biologically active derivative or fragment thereof in the preparation of a medicament, said medicament having complement inhibitor activity, for treatment or prophylaxis of a reperfusion injury in a subject in need of treatment by administering to the subject a therapeutically effective amount of said medicament.

The subject may be a mammal, preferably a human.

The VCP polypeptide may be administered prior to or during reperfusion of the coronary artery and may be administered as a single bolus treatment.

The VCP complement inhibitor activity may comprise inhibiting formation of an active C3 convertase, promoting inactivation of the active C3 convertase, inhibiting conversion of a C3 molecule to a C3b molecule, or combinations thereof.

The C3 convertase may be a classical pathway C3 convertase or an alternative pathway C3 convertase.

It will be understood that various details of the presently disclosed subject matter may be changed without departing from the scope of the subject matter disclosed herein. Furthermore, the foregoing description is for the purpose of illustration only, and not for the purpose of limitation.

The invention is now described, by way of example, with reference to the following Examples and FIGS., in which:

FIGS. 1*a*, 1*b* and 1*c* show respectively (a) longitudinal section of the whole mouse heart with the aorta (arrow); (b)

and (c) higher magnifications of the aorta with valve leaflet (arrowhead) [(a) and (b) Masson gold trichrome, (c) Orcein].

FIGS. 4a, 4b, 4c and 4d show respectively atherosclerotic lesions in the aorta of a mouse fed with high-fat diet for 15 weeks. Sections stained in parallel with oil-red O (a) and immunohistochemistry (b-c) show the entry of macrophages (arrows) into the lesion encircled in (a). Note the accumulation of foam cells in the intima which lead to aortic lesions (arrowhead); (d) positive immunohistochemical reaction of the intima and adventitia.

Figure 5A:
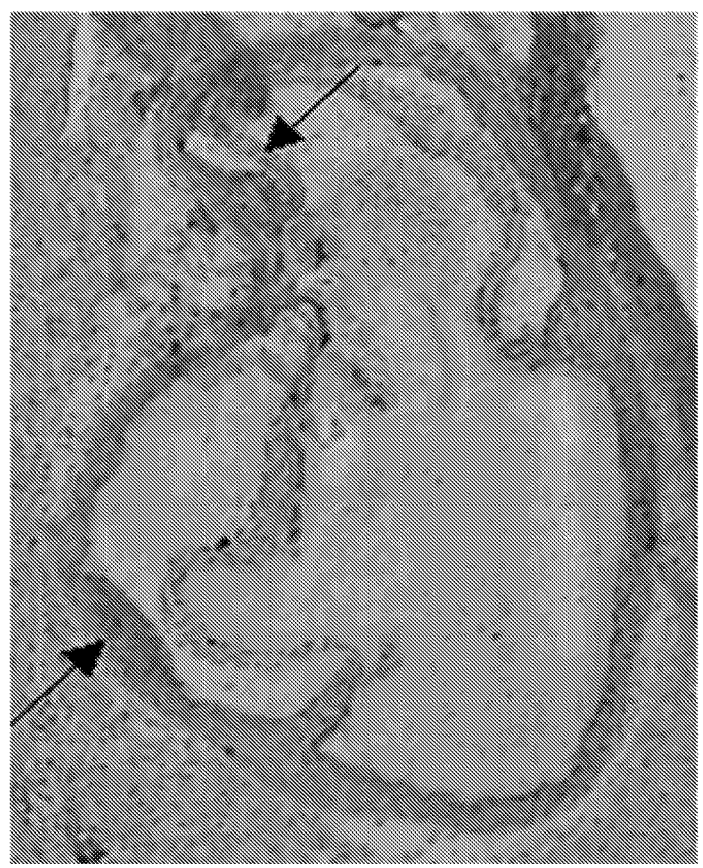
Figure 5B:
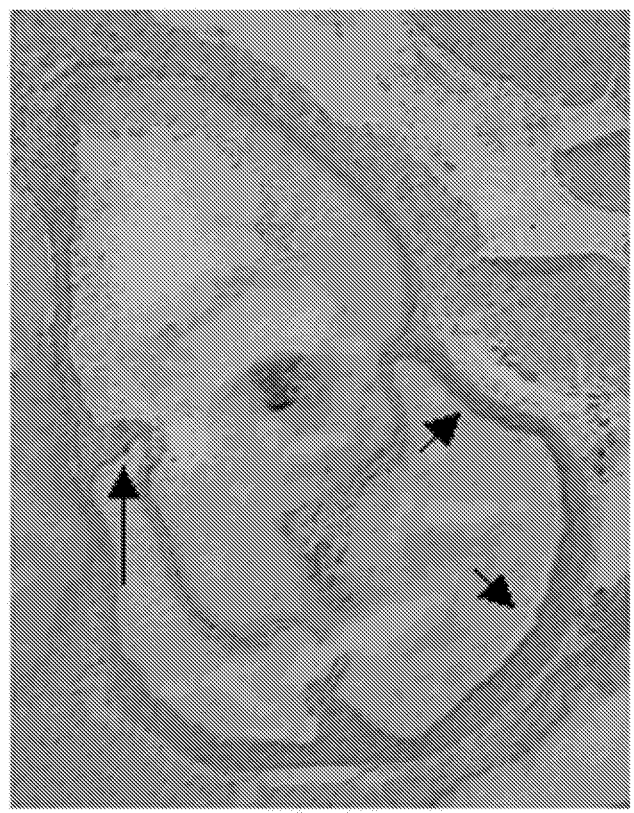
Figure 5C:

FIGS. 5a, 5b and 5c show respectively the development of fatty streaks in mice fed with high-fat diet for 15 weeks and injected with saline (a) or 20 mg/kg VCP (b) in week 8-15. The lipid plaques are shown by arrows in the intima (b) or intima and media (a). No lipid staining is evident in a mouse fed with chow diet and injected with saline (c) (oil-red O staining).

Figure 6:
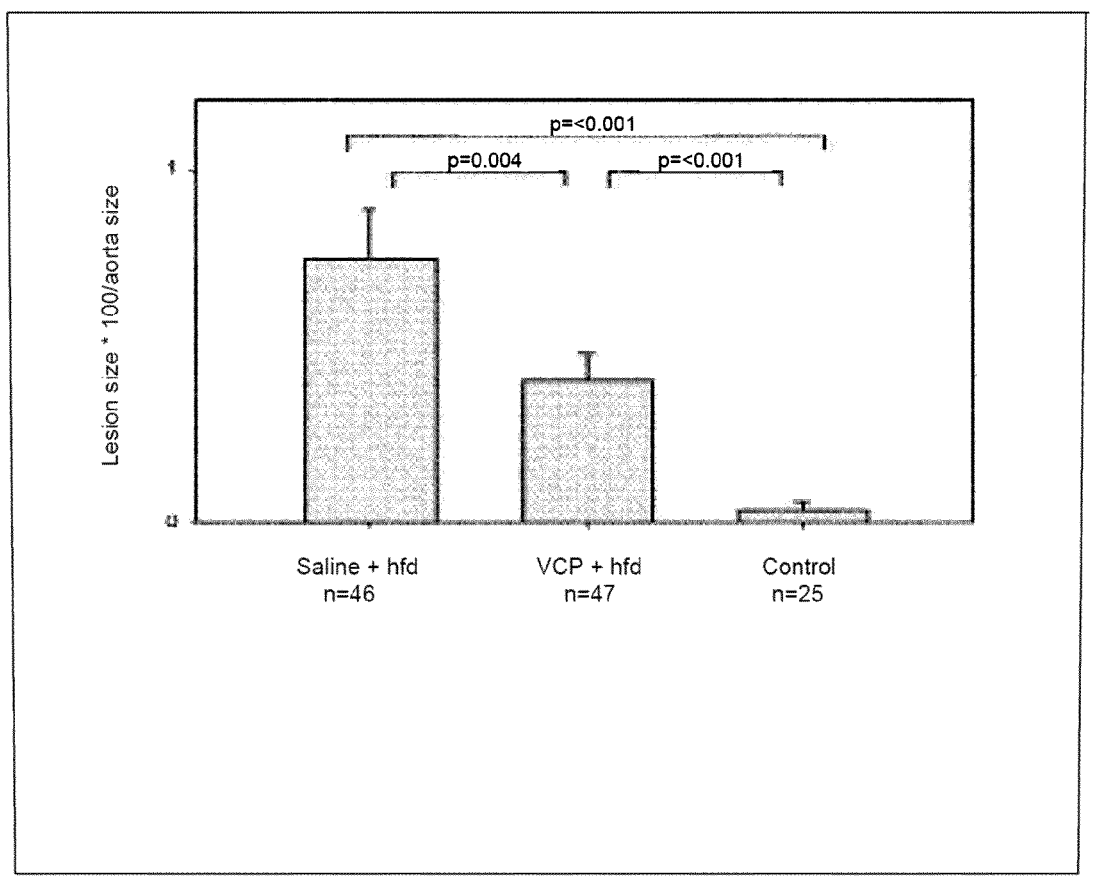

FIG. 6 shows percent lesion area in aortic sections from mice a) fed with high fat diet and injected with saline (N=10), b) fed with high fat diet and injected with 20 mg/kg VCP (N=10) and c) control mice (N=3); the number (n) of sections examined is indicated on the x-axis.

Figure 7:
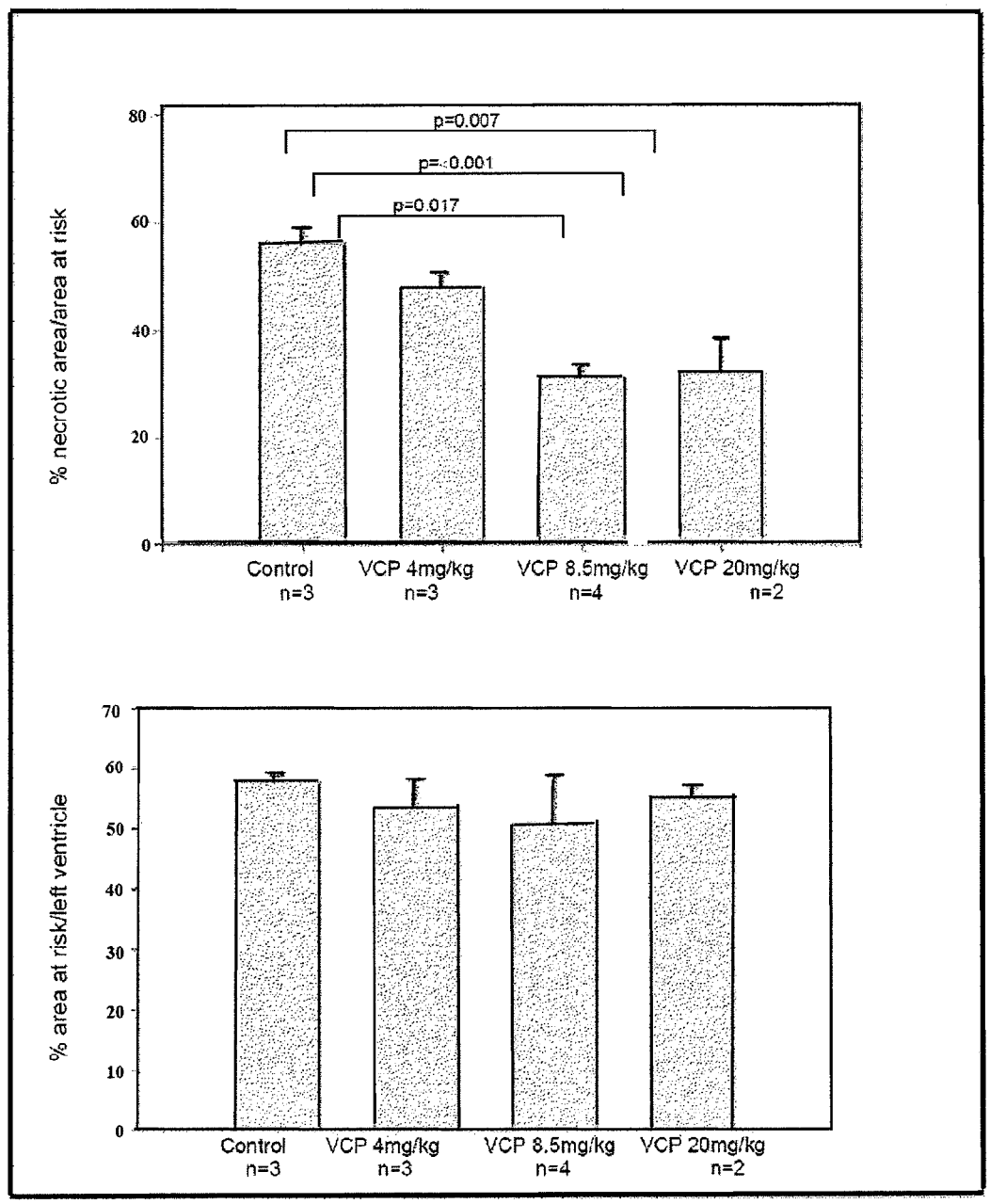

FIG. 7 shows infarct size in rats after ischemia-reperfusion. The figure on the top shows percent infarct size expressed as percent of the area at risk. The infarct size is shown in rats after ischemia-reperfusion treated with a) saline; b) 4mg/kg VCP, p=0.017, c) 8.5 mg/kg VCP, p<0.001 & d) 20mg/kg VCP, p=0.007. The figure on the bottom shows the area at risk expressed as percent of the left ventricle in I/R rats treated with a) saline; b) 4mg/kg VCP, c) 8.5 mg/kg VCP & d) 20mg/kg VCP.

EXAMPLE 1

Materials and Methods

Animals

Atherosclerosis was induced in female C57BL/6J mice by feeding them with high-fat diet. The C57BL/6 mouse strain is very susceptible for developing diet-induced atherosclerosis. Control mice were fed with chow diet. The mice were 5-6 weeks old at study initiation, weighing on average 16-18 g. The study was approved by all relevant animal care committees.

Materials

Female C57BL/6J mice were purchased from Jackson (Maine, USA), high-fat diet from ICN (Irvine, Calif., USA) and chow diet from Special Diet Service (Witham, UK). VCP was produced in recombinant form in yeast (see below). Heparin columns (5 mL HiTrap™) were from Amersham (Uppsala, Sweden) and endotoxin removing columns (1 mL Detoxi-Gel™) from Pierce (Rockford, Ill., USA). Bovine serum albumen (BSA), Coomassie blue, orcein, hematoxylin and eosin were from Sigma (St. Louis, Mo., USA), Tris and $H_2O_2$ from Merck (Darmstadt, Germany), O.C.T.™ from Sakura Finetek (Zoeterwoude, Netherlands), glycergel mounting medium from Dako (Copenhagen, Denmark), diaminobenzidine from Pharmingen-BD (San Diego, Calif., USA), and EZ complement kit from DiaMedix (Miami, Fla., USA). Complement fixation test diluent (CFD) was from Flow Laboratories (Irvine, Scotland), oil-red O and HRP-conjugated goat anti-rat IgG from ICN, and monoclonal rat anti-mouse MOMA-2 from Serotec (Oxford, UK).

Production and Purification of VCP

The cloning of VCP in the *Picia pastoris* yeast expression system (Invitrogen) was according to known procedures. Two mL of buffered minimal glycerol (BMG) were inoculated and grown overnight at 30° C. This starter culture was then used to inoculate 2L of BMG and the cultures grown for two days at 30° C. with vigorous shaking The cells were harvested by centrifuging (3500 rpm, 30 min), resuspended in 2L of buffered minimal methanol (BMM) containing 4% methanol, and incubated for two days with vigorous shaking The VCP-containing medium was then collected after centrifuging (12,000 rpm, 1 h) and the two liters concentrated to 50mL using a 300mL Amicon- stirred cell with 10 kDa molecular weight cut-off (Millipore, Billerica, Mass, USA). Half of the medium was then passed at a rate of 1mL/min through three 5mL heparin columns linked in series, and after washing with 30mL of 100mM NaCl, the protein was eluted with 15mL NaCl ranging from 250mM to 550mM. The fractions were visualized by SDS-PAGE (Invitrogen) with Coomassie blue staining This was repeated for the second half of the medium and VCP fractions were pooled, concentrated in a 50mL Amicon stirred- cell, and superconcentrated and desalted using several 2mL centrifugal filters (Centricon, Millipore). Protein concentrations were assayed using a protein estimation kit (BioRad, Hercules, CA, USA), and the specific activity of the samples determined by hemolysis assay (see below). Purified VCP is very resistant to adverse conditions but for convenience it was transported as lyophilized product. Before use it was restored in distilled water, purified by passage through a heparin column and endotoxin removing gel. Briefly the VCP, which has heparin binding capabilities (Smith et al, 2000a), was passed through a 5mL HiTrap Heparin column (Amersham, Uppsala, Sweden) and the void volume, containing endotoxin and other contaminants was discarded. Binding of VCP to the column was ensured by using binding buffer (solution of 10mM sodium phosphate $Na_3PO_4$) and 10mM potassium phosphate $KH_2PO_4$), pH 7) and eluted by using salt solution (elution buffer; binding buffer (see above) containing 1-2M NaCl ). The column was operated using a pump, flow rate 60mL/hour, and the protein was detected using a UV monitor (Pharmacia LKB Biotechnology, Bromma, Sweden). Prior to use all buffers and samples were degassed in vacuum.

An endotoxin-removing column (1 mL Detoxi-Gel™ from Pierce, Rockford, Ill., USA) was used to remove any residual endotoxin. The endotoxin binds to the column while the VCP flows through. The endotoxin was bound to the column by using salt buffer (10 mM sodium phospate buffer with 0.5 M NaCl, pH 7) and eluted (in order to make the column available for further use) by using 1% sodium deoxycholate (Sigma, St. Lous, Mo., USA). After purification, the VCP was concentrated by freeze-drying and resolved to 2.2 mg/mL in 0.9% saline.

VCP Pharmacokinetics

The pharmacokinetics of injected VCP was followed in four mice injected i.p. with 10 mg/kg VCP. Blood was sampled from the tail vein at 1, 3 and 7 hours, and at 1 and 4 days. The EZ Complement CH50 kit was used to measure the VCP inhibition. The sensitized cells were concentrated 2× by decanting half of the buffer, and allowed to equilibrate to room temperature. Each test involved 75 μL of sensitized red blood cells, 15 μL of mouse serum and 10 μL CFD. Results were expressed as percent of a positive control (red blood cells lysed with $H_2O$). One tube was used for spontaneous lysis. The tubes were incubated at 37° C. for 1 hour and centrifuged at 150 g for 5 min. Absorbances were read at 405 nm.

Experiments

The study included three groups of mice; a) 10 mice fed with high-fat diet and injected with VCP (study group), b) 10 mice fed with high-fat diet and sham-injected with 0.9% saline (disease control group), and c) 10 mice fed with chow diet and injected with saline (negative control group). Mice were injected in the tail vein with VCP or saline at weekly intervals from week 8 to week 15. At the end of the experiment the mice were killed by cervical dislocation and the hearts excised. This experiment was designed to make optimal use of the available VCP; 15 weeks on atherogenic diet are sufficient for fatty streak development and this development occurs primarily after 7-8 weeks as confirmed in a preliminary experiment.

Histology

The normal structure of the heart was studied in longitudinal sections of whole formalin-fixed hearts stained with haematoxylin and eosin (HE), orcein or Masson gold trichrome. For evaluation of atherosclerotic lesions, the lower half of the heart was discarded after being cut parallel to the atria. The upper half of the heart was mounted in O.C.T., quick frozen in liquid nitrogen, and kept at −70° C. Sections were obtained by conventional methods. Briefly, the tissue blocks were trimmed on a cryotome (Reichert-Jung, Cambridge, UK) and then cut at 10 μm beginning with the lower portion of the heart. Sections were discarded until the three valve cusps were visible, and sections were then retained until the aorta was round and muscular and valve cusps no longer visible. Every sixth section was kept for immunohistochemical staining; the remaining sections were stained with oil- red O and counterstained with hematoxylin.

Immunohistochemistry

Cryostat sections were air-dried and fixed with acetone. Macrophages were visualized by rat anti-MOMA-2 (incubated overnight) after pretreatment for 10 min. in 3% $H_2O_2$ in Tris (to block endogen peroxidase) and 20 min. in a mixture of rat serum and 1% BSA in Tris (to avoid non-specific antibody reaction). The anti-MOMA-2 antibody was detected with HRP-conjugated goat antibody against rat IgG (30 min.) and visualized with diaminobenzidine (10 min). Hematoxylin was used for counterstaining.

Evaluation of Atherosclerotic Lesions

Evaluation of atherosclerotic lesions was confined to the 280 μm interval just beyond the aortic sinus and at the beginning of the aorta, and based on every fourth section as described by Paigen et al. For objective analysis of the atherosclerotic progression, a photomicroscope attached to a digital camera (Leica, Bensheim, Germany) was used. The Leica Qwin program was used for computer analysis of images, and to minimize experimental error, lesion size was expressed as % of the circumference of the aorta in the section examined. The sections were evaluated in a blinded fashion.

Statistical Analysis

Percent lesion size from the aortic root area (lesion size*100/aortic circumference) was compared between the three experimental groups using the Mann-Whitney rank sum test. Significance was set at $p<0.05$.

Results

Normal Structure of Mouse Heart

Figure 1A:
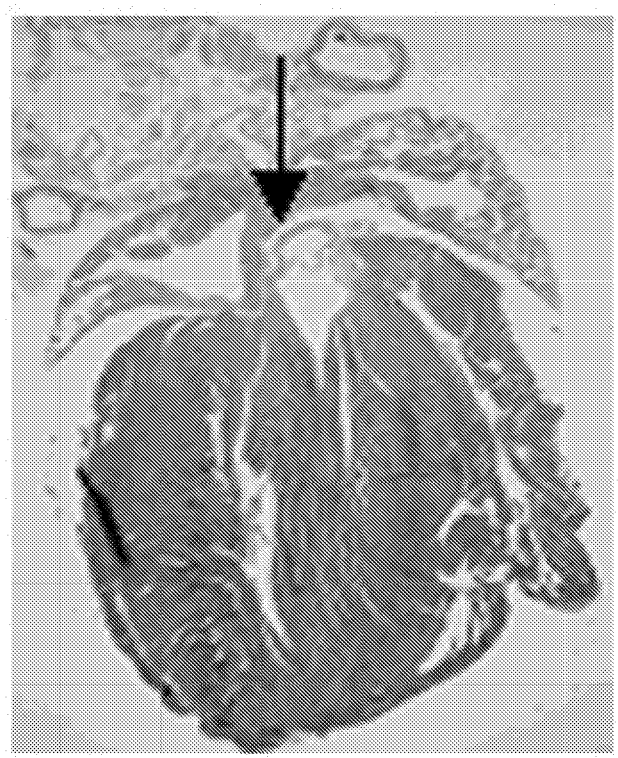
Figure 1B:
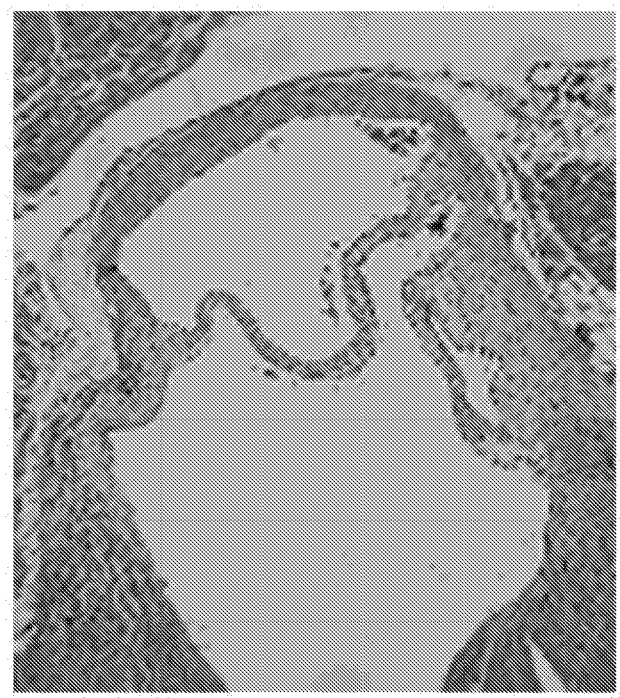
Figure 1C:

FIG. 1 shows the normal anatomy of the mouse heart. The aorta is evident at the base of the right atrium (arrow). One of the three valve leaflets is visible (arrowhead). The valve is rich in collagen as seen with the Masson gold staining (FIGS. 1a and b), but the aortic wall is mostly composed of fibrotic tissue, which stains prominently with orcein (FIG. 1c).

Atherosclerotic Lesions

Figure 2A:
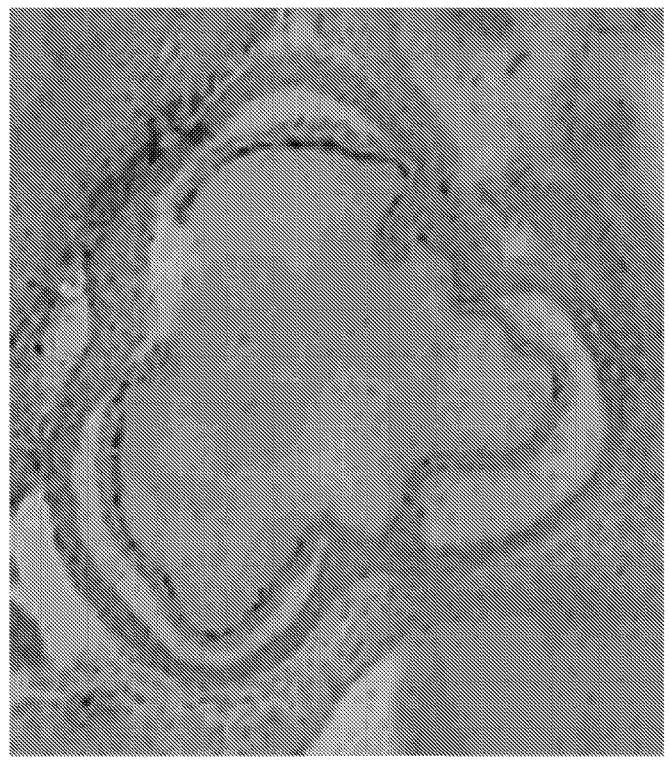
FIGS. 2a, 2b and 2c show respectively cross sections of the aorta, showing the beginning (a), middle (b) and end (c) of the 280 μm interval studied (oil-red O). All three valves are still visible in (a) while only the cusps are showing in (b); in (c) they are disappearing and the aorta is almost round in shape with the wall becoming muscular.
Figure 2B:
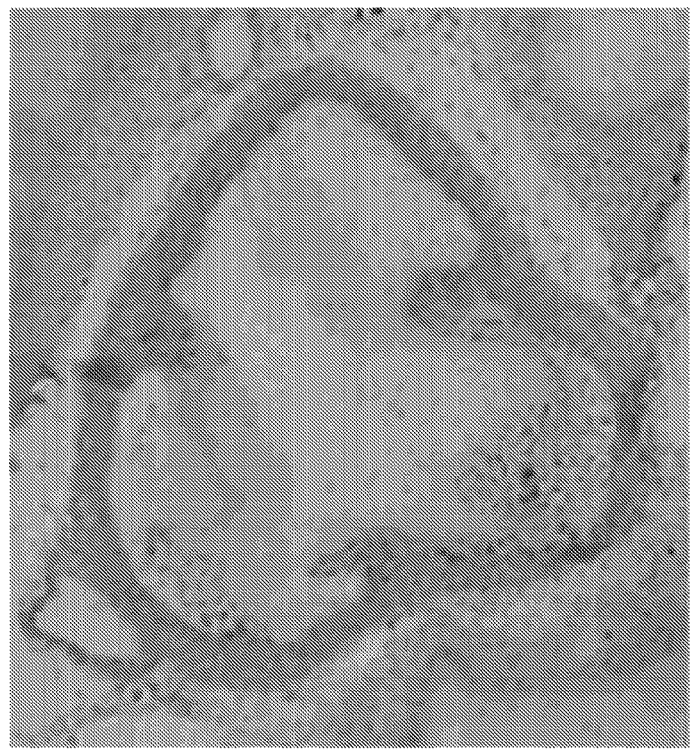
Figure 2C:
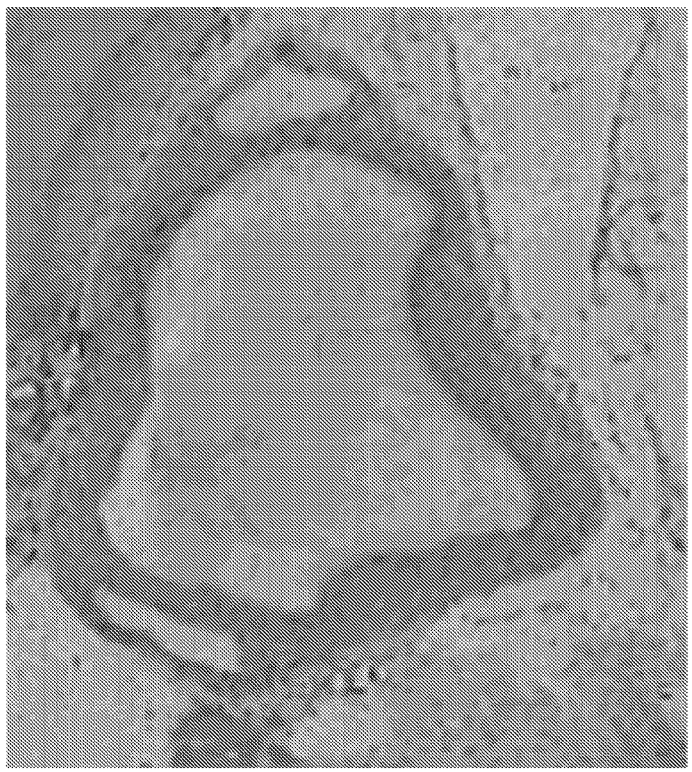
Figure 3A:
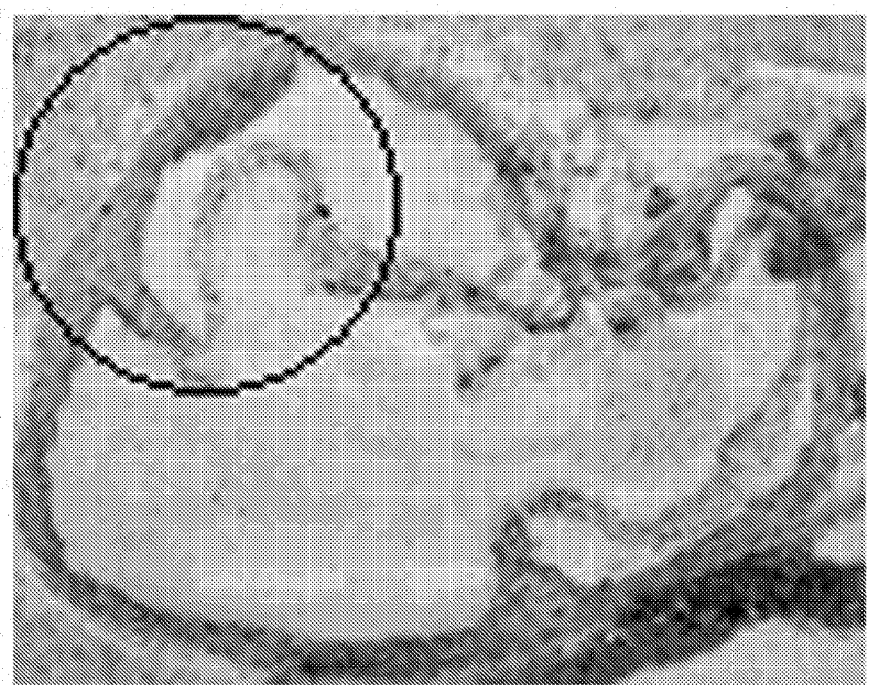
FIGS. 3a, 3b and 3c show respectively fatty streaks in the aorta of a mouse fed with high-fat diet for 15 weeks (oil-red O); (a) overview, (b-c) magnification of the circled area. Fatty streaks are typically seen in the semilunar valve (b) and the aortic wall (c) where lipids are deposited in the tunica intima but even more prominently in the tunica media.
Figure 3B:
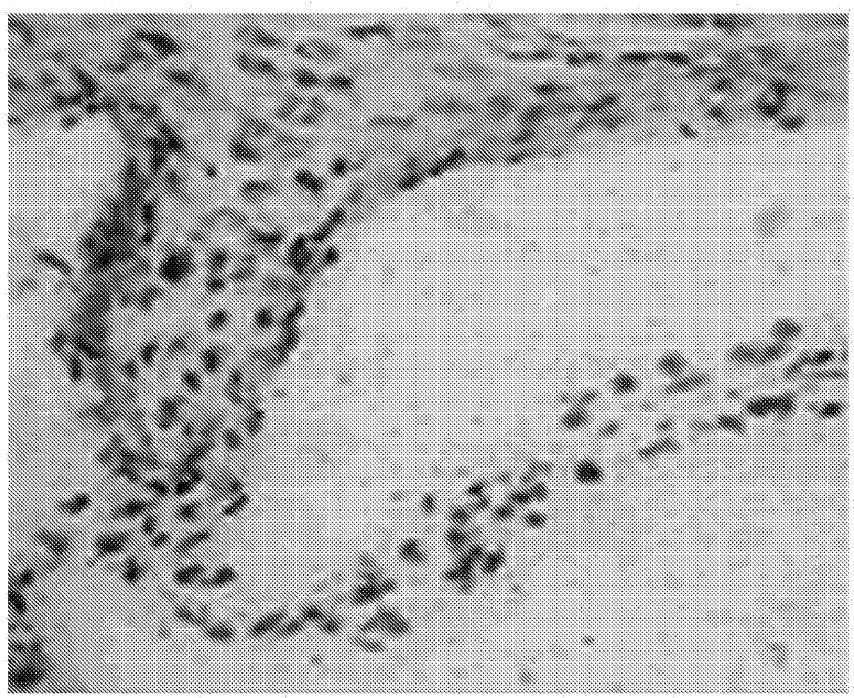
Figure 3C:
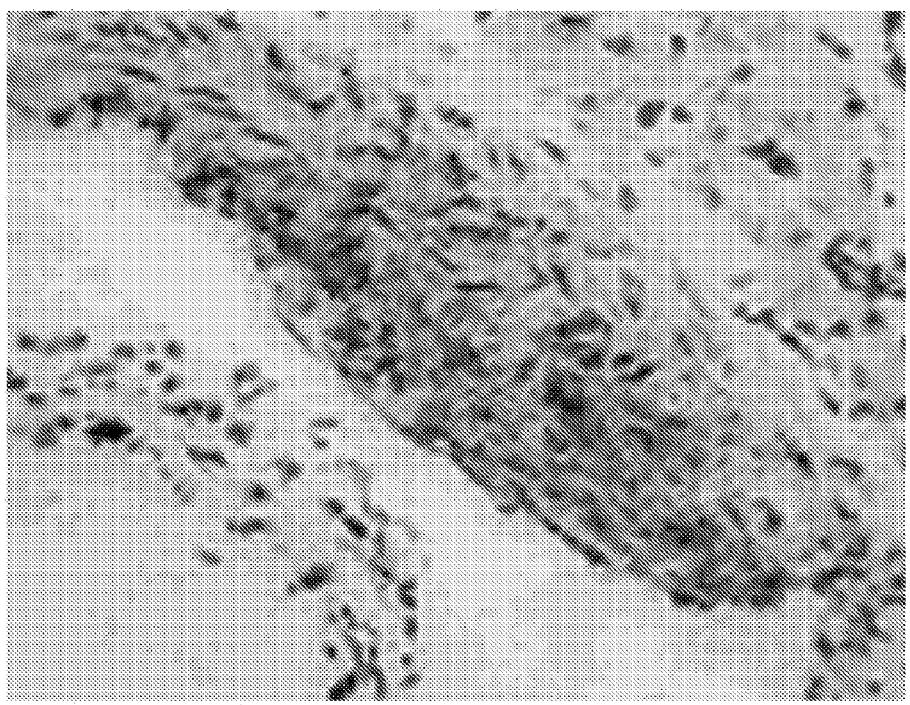
Figure 4A:
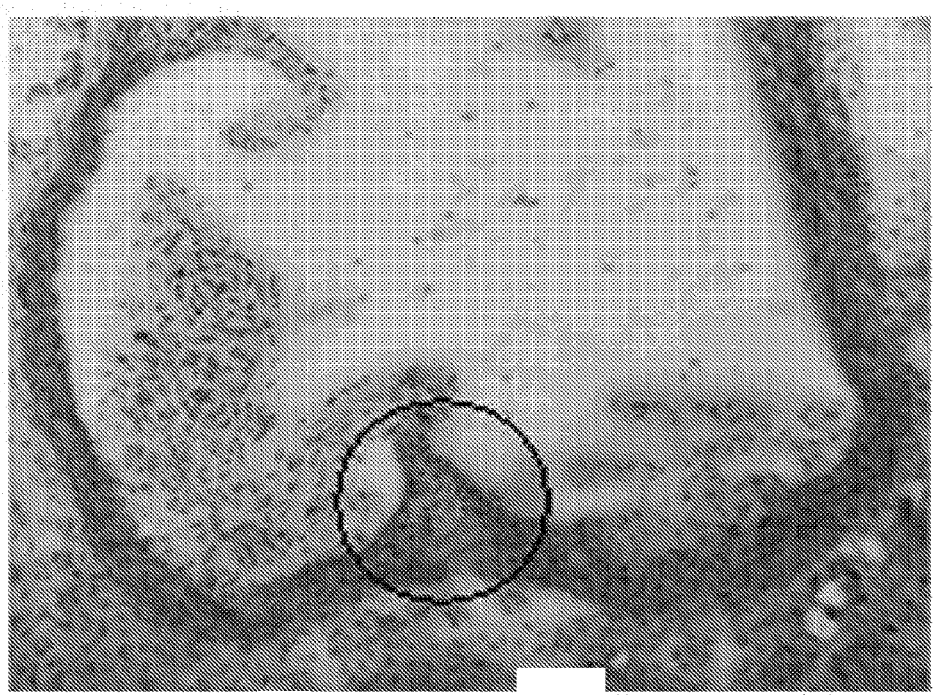
Figure 4B:
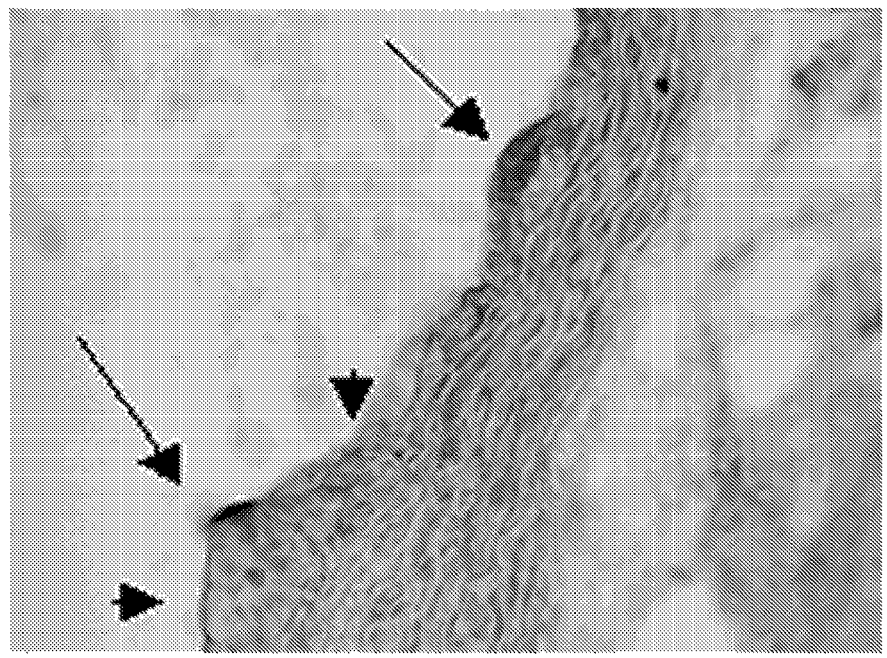
Figure 4C:
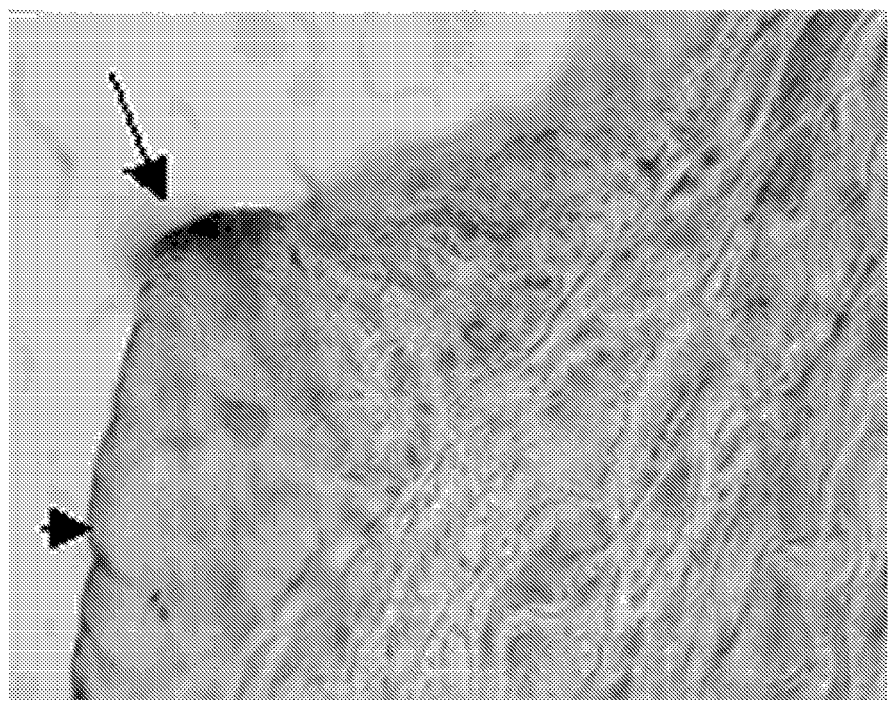
Figure 4D:

After 15 weeks on atherogenic diet, cross sections of the 280 μm interval between the aortic sinus and the beginning of the aorta (FIG. 2) showed atherosclerotic lesions composed of oil-red O positive lipid deposits (FIG. 3). These lesions did not progress beyond the fatty streak stage during the course of the experiment. Lipid deposition was not confined to the intima but extended far into the media (FIG. 3c), as no internal elastic lamina separates these layers in this part of the aorta. Lesions were also commonly seen in the base of the semilunar valve (FIG. 3b). The presence of macrophages in fatty streaks was verified by immunohistochemical staining of sections cut in parallel with oil-red O stained sections (FIG. 4).

Quantitative Analysis of Atherosclerotic Lesions

The injection of VCP led to reduction in serum hemolytic activity from 50% to 40%; the effect was however delayed in mice injected i.p. with a peak at 24 h. VCP activity had disappeared after 4 days. Evaluation of lesions in mice fed on atherogenic diet for 15 weeks and injected at weekly intervals in the last 7 weeks with either VCP or saline indicated a significant reduction in size in the VCP-injected mice, compared to the saline-injected mice (FIG. 5). This was confirmed by computer-assisted evaluation of digital images captured by the Qwin program (p=0.004, FIG. 6). No lesions were evident in control mice fed with normal diet (FIG. 5c). No differences were observed in food intake or weight between the groups (results not shown). Mortalities were similar in experimental and control groups (2 and 3 mice respectively).

EXAMPLE 2

Materials and Methods

Purification of VCP. Production and purification of VCP in recombinant form by using the Picia pastoris yeast expression system was according to known procedures. The lyophilized product was reconstituted in $dH_2O$ and purified by passage through a heparin column and endotoxin removing gel.

Rats

The study involved 4-6 months old Sprague-Dawley rats, weighing on average 250-350 g. The animals were randomly divided into 4 groups; group (a) received 20 mg/kg VCP (n=2), group (b) 8.5 mg/kg VCP (n=4), group (c) 4 mg/kg VCP (n=3) and the control group (d) was injected with saline (n=3). Myocardial infarction was experimentally induced in all rats by surgical ligation of the left anterior descending coronary artery (LADCA), and the size of reperfusion injury measured and compared between groups. The study was approved by all relevant animal care committees.

Surgical Procedure

The surgical procedure is well established. In brief, the rats were anaesthetized with urethane (1.25 g/kg i.p.) (Sigma-Aldrich, Milan, Italy) and then fastened on a glass plate with adhesive tape. A catheter for VCP/saline injection was then inserted into the femoral vein and the thoracic artery cannulated for blood pressure measurements (the normal blood pressure of a rat is 90 mmHg). A tracheotomy was performed and the animal was connected to a ventilator (Ugo Basile 7025 rodent ventilator, 54 strokes pr. min). A left thoracotomy was performed between the fourth and fifth ribs, the ribs cut and the pericardium removed for easier access to the heart.

The heart was exteriorised and a fine silk ligature placed around the left anterior descending coronary artery by using a 10 mm micropoint reverse cutting needle (Pomezia, Rome, Italy). After the surgical procedure the rat was allowed to recover for 20 minutes before continuing. Coronary artery occlusion was achieved by threading the ligature through a plastic button, which was then pressed down against the heart and the ligature fastened with an artery clip. Ischemia was allowed for 30 minutes, but 5 minutes before reperfusion, VCP (4, 8.5 or 20 mg/kg) or saline was injected into the femoral vein. After 30 min. of ischemia, the clip was removed with the tension of the ligature released, and reperfusion allowed for 3 hours.

After the reperfusion period the coronary artery was re-occluded and 1 mL Evans blue dye (Sigma-Aldrich), 2% w/v, injected through the thoracic artery. The dye stains the perfused myocardium, while the occluded tissue remains uncoloured, and thus the ischemic area (area at risk, AR) is negatively stained. The heart was then removed and put in saline to remove excess dye. The right ventricle was removed along with the stained part of the left ventricle, which represents the non-ischemic area. The ischemic, (AR, unstained, pink) and the non-ischemic (blue) part of the left ventricle were weighed and compared. The area at risk was expressed as percent of the total left ventricular weight.

To distinguish between injured (necrotic) and unharmed (non-necrotic) ischemic myocardium, the area at risk was cut into small pieces with a scalpel and incubated with 0.5 mg/mL p-nitro-blue tetrazolium (NBT) (Sigma-Aldrich) at 37° C. for 10 min. NBT stains living tissue, with intact dehydrogenase enzyme. The stained tissue (dark blue, representing non-necrotic tissue) and the unstained tissue (pink, necrotic tissue) were separated and compared by weighing. The injured (necrotic) tissue was expressed as percent of the area at risk (AR), and the area at risk as percent of the left ventricle.

Statistical Analysis

Percent necrotic area/area at risk (NA/AR) and area at risk/left ventricle (AR/LV) was calculated and compared between groups using t-test. P values below 0.05 were considered significant. The statistical analysis was done by using the SigmaStat 2.01 software (Jandel Scientific).

Results

The size of the infarcted area after reperfusion of ischemic myocardium is a good indicator of myocardial injury. To determine the protective effect of VCP on myocardial damage and to find the appropriate dose of VCP, i.v. injection of VCP (4mg/kg and 20mg/kg) or saline was made after 25 minutes of ischemia, i.e. 5 minutes prior to reperfusion. The necrotic area was 56 +/−2.5%, 48 +/−2.5% and 32 +/−6% for the saline treated (control), VCP 4mg/kg-treated and VCP 20mg/kg-treated rats respectively (Table 1). By extrapolation, 8-12mg/kg were calculated to offer maximal protection, and this was verified by repeating the experiments using 8.5mg/kg, giving a necrotic area of 31 +/−2%. Treatment with VCP in the higher doses 8.5mg/kg and 20 mg/kg) 5 min. before reperfusion reduced the size of the infarcted area by of 44% and 43% respectively compared to the saline treated rats (p<0.001 and 0.007 respectively). At an even lower dose, 4 mg/kg, there was also a significant reduction (14%, p=0.017) in the size of the infarcted area compared to saline injected rats (FIG. 7). The area at risk was essentially the same in all rats (Table 1, FIG. 7). Thus it is evident that VCP injection reduces the size of the infarcted area in a rat myocardium after ischemia/reperfusion in a dose dependent manner.

TABLE 1

Average size of the necrotic area and the area at risk in rats after reperfusion injury.

| Group | number | % necrotic area/ area at risk | % area at risk/ left ventricle |
|---|---|---|---|
| Saline | 3 | 56 | 58 |
| VCP 4 mg/kg | 3 | 48 | 54 |
| VCP 8.5 mg/kg | 4 | 31 | 51 |
| VCP 20 mg/kg | 2 | 32 | 55 |

Discussion

The invention shows that the development of fatty streaks in an animal model of diet-induced atherosclerotic disease can be significantly retarded by the injection of a complement inhibitor, VCP. Previous studies had demonstrated that (a) complement is deposited in atherosclerotic lesions from patients as well as experimental animals, (b) activation of complement is the first sign of inflammation in the arterial wall in animal models of atherosclerosis, taking place concurrently with LDL deposition and before monocyte recruitment and (c) the concentration of terminal complement complex C5b-9, a marker of complement activation, increases in parallel with lesion progression. An apparent controversy however existed over the relative importance of complement in this scenario since (d) in C6-deficient rabbits fed with high-fat diet, complement appeared to play an obligatory and rate-limiting role but (e) in genetically modified mice (LDLR-/- and/or ApoE-/-), deficiency of complement (C3 or C5) did not retard lesion progression. Deficiency of C5 in ApoE-/- mice did not lead to any visible changes, while deficiency of C3 in LDLR-/- or LDLR-/- ApoE-/- mice led to increased lesion size, with increased build-up of LDL and macrophages and slower transition from fatty streaks to fibrotic plaques in the former mouse strain. To account for the controversy between findings (c) and (d), it had been suggested that the process of atherogenesis might differ between animal species or between genetically driven and diet-induced disease. The invention indicates the latter supposition, as mice of the same strain (C57BL) as previous experiments, were used only without genetic modifications. The invention supports the view of complement as an obligatory step in diet-induced atherogenesis, unless the disease is driven by major defects in lipid metabolism.

After 15 weeks on atherogenic diet, lipids and macrophages were abundant in lesions, but lesions did not progress beyond the fatty streak stage. This is consistent with previous observations on the C57BL/6 mouse model. Staining was not specially for smooth muscle cells (SMC) but normal histology showed no SMC in the intimal layer of the aorta. The observation that lesions do not progress beyond the foam cell stage, and that lesions are significantly smaller in VCP injected mice supports previous data suggesting that complement activation is important in the first stages of lesion formation of diet-induced atherosclerosis. Due to its heparin binding sites, VCP may be sequestered in the body for periods exceeding its half-life in serum, and this may explain the relatively high level of protection attained even by weekly injections. It is however likely that the 50% protection observed is a compromise of a much higher level of protection immediately after injection and no or lower protection towards the end of the week. Combined with the observation that total deficiency of C6 resulted in complete inhibition of fatty streak development in rabbits, the results suggest that a much higher level of protection may be achieved with changes in injection regime. Several studies have previously suggested a beneficial effect of VCP or other complement inhibitors in xenotrans-plantation, Alzheimers disease, brain and spinal cord injury and reperfusion injury, but the focus had been mainly on therapeutic use. From a wider point of view, the invention suggests that complement may be a rate-limiting step in diet-induced disease, although in disease driven by defects in lipid metabolism it may be redundant.

Complement may become activated directly by modified LDL present in the forming plaque. It could also become activated by immunoglobulins or C-reactive protein (CRP); IgM and IgG are retained in the atherosclerotic lesions and can form immune complexes with oxLDL. CRP deposition has also been confirmed in human atherosclerotic lesions and found to be consistent with the severity of the lesion. CRP may modify the outcome by limiting the activation to the C3 level, as evidence has shown that it prevents the formation of MAC but favours opsonization. The presence of C5b-9 (MAC) in the deeper layers of human lesions however suggests that the effect of CRP may be confined to the upper layers where the activation takes place and that CRP and/or MAC inhibitors are less abundant in the deeper layers. Complement activation may modulate lesion development in various ways. Generation of anaphylatoxins may play a part in leukocyte recruitment. Generation of C5b-9 within the arterial wall may injure vascular cells triggering the release of growth factors and cytokines from endothelial cells, macrophages and SMC. Of these cells, smooth muscle cells are the most likely target for C5b-9 formation because they are poorly protected by complement regulatory proteins. Such attack on SMC with release of MCP-1 might explain the initial monocyte recruitment into the arterial wall. It might in fact also explain SMC proliferation in the lesion as sublytic attack of MAC has been shown to be mitogenic for SMC. Complement activation is associated with apoptosis. C5b-9 deposits in atherosclerotic lesions are localized not only on intact SMC and on cell debris but also on apoptotic cells, indicating that activation of the complement system by apoptotic cells may contribute to lesion development. Complement activation may thus play a role in both fatty streak formation and in the chronic inflammatory processes involved in lesion progression.

The findings of 50% protection against fatty streak formation in wild-type C57BL mice by weekly injections of VCP, combined with previous data implicate complement activation as a rate-limiting step in lesion formation in diet-induced atherosclerotic disease.

The invention shows that complement plays an important role in lesion formation in diet-induced atherosclerosis. The invention also confirms the importance of complement in reperfusion injury. The invention clearly demonstrates the effectiveness of the complement inhibitor, VCP, in reduction of reperfusion injury after coronary artery ligation.

Administration of VCP just prior to reperfusion of rat myocardium was found to reduce reperfusion injury in a dose dependent manner. At higher doses nearly 50% protection was attained. VCP inhibits all three activation pathways of complement making it highly effective in reducing reperfusion injury which is known to involve activation of complement through all three activation pathways.

The mechanism by which the complement system is activated in ischemia-reperfusion is not fully understood. The complement components C1q, C3, C4 and C5 are found in abundance in infarcted tissue, and increased plasma levels of C3d, C4d, Bb and sC5b-9 have been detected in patients with acute myocardial infarction (AMI). It has been shown that the presence of C5b-9 in necrotic tissue is associated with loss of CD59, which is released from sarcolemmal membranes. Previous studies suggest that the heart is less protected against the early than the late complement cascade, because the regulators of the C3/C5 step (CR1, DAF, MCP) are absent or expressed in low levels in cardiomyocytes, whereas regulators of MAC (CD59 and C8BP) are strongly expressed. This implies that during AMI the contact of plasma with insufficiently protected cardiomyocytes may lead to generation of the classical and alternative pathway C3/C5 convertases (while MAC attack on SMC in vivo occurs because of absent or low expression of CD59 by SMC). Upon reperfusion, the blood contact with damaged and foreign endothelium will lead to a certain degree of activation of the complement system. Binding of auto-antibodies to epitopes on endothelial cells or other arterial constituents, or deposition of immune complexes on cytoskeletal elements could activate the complement cascade. C1q has been shown by previous studies to bind to subcellular constituents of cardiac muscle such as membrane particles and mitochondrial membranes, and to natural antibodies through the Fc region, and is thereby capable to activate the complement cascade during MI. C-reactive protein (an acute phase protein), a potent activator of the classical pathway, is in increased concentrations in serum after AMI and it is found deposited with activated complement on myocardial cells in the infarcted area. Recent studies indicate that activation of the lectin pathway is a rate-limiting step in reperfusion injury.

The activation of the complement system can lead to the production of the chemotactic and vasoactive products C3a and C5a which trigger inflammation in the ischemic lesions by inducing neutrophil attraction, aggregation and secretion of radicals, and the activation can lead to the deposition of the MAC. C5a induces the fusion of intracellular vesicles containing the adhesion molecule P-selectin with the surface of the endothelium and also the synthesis of cytokines (IL-1, IL-6 and TNF-$\alpha$) which can induce the expression of ICAM-1 and E-selectin. In addition, C5a acts as a chemoattractant for neutrophils. MAC does not likely cause lysis of nuclated cells, but loss of CD59 in myocardium may lead to full assembly of MAC in the myocardial tissue, to occur between 6 hrs. and 3 days. MAC can induce numerous cellular responses in the absence of cell death in the ischemic tissue. It can cause endothelial activation, causing increased expression of cell adhesion molecules (P-selectin, E-selectin, ICAM-1 and VCAM-1) which facilitate neutrophil adherence, and it can activate the endothelium to release IL-8 and MCP-1 and other factors which are chemotactic for neutrophils and cause increased vascular permeability. Activated endothelium can also release growth factors and trigger SMC migration and proliferation. In addition MAC can trigger SMC to release MCP-1. Complement activation may thus play an important role in inflammatory response and transcellular migration of leukocytes during ischemia-reperfusion.

In conclusion activated complement has a major impact on myocardial tissue damage during reperfusion injury. The invention demonstrates that 50% protection is attainable against fatty streak formation in a mouse model, C57BL/6, by weekly injection of a complement inhibitor, VCP. This finding implicates complement activation as a rate-limiting step in lesion formation in diet-induced atherosclerotic disease and increases the understanding of the disease course. The invention further shows that the myocardial-tissue damage formed during ischemia-reperfusion by the complement system can be reduced by ~50% with the use of VCP.

The invention claimed is:
1. A method of treating atherosclerosis, comprising:
administering to a subject in need of treatment for atherosclerosis a therapeutically effective amount of a comple- ment inhibitor, wherein the complement inhibitor is a vaccinia virus complement control protein (VCP) or fragment thereof.

2. The method of claim 1, wherein the subject is a mammal.

3. The method of claim 2, wherein the subject is a human.

4. The method of claim 1, wherein administering to the subject the complement inhibitor comprises intravenously injecting into the subject the complement inhibitor.

5. The method of claim 1, wherein the therapeutically effective amount of the complement inhibitor ranges from about 0.01 g/kg to about 0.1 g/kg per dose.

6. A method of inhibiting the production or progression of one or more atherosclerotic lesions within the vasculature of a subject, comprising:
administering to a subject having one or more atherosclerotic lesions a therapeutically effective amount of a complement inhibitor, wherein the complement inhibitor is a vaccinia virus complement control protein (VCP) or fragment thereof.

7. The method of claim 6, wherein the subject is a mammal.

8. The method of claim 7, wherein the subject is a human.

9. The method of claim 6, wherein administering to the subject the complement inhibitor comprises intravenously injecting into the subject the complement inhibitor.

10. The method of claim 6, wherein the therapeutically effective amount of the complement inhibitor ranges from about 0.01 g/kg to about 0.1 g/kg per dose.

11. The method of claim 6, wherein the vasculature comprises a cardiac artery.

12. The method of claim 11, wherein the vasculature comprises an aorta.

13. A method for treating a reperfusion injury, comprising:
administering to a subject in need of treatment for a reperfusion injury a therapeutically effective amount of a vaccinia complement control protein (VCP) or fragment thereof.

14. The method of claim 13, wherein the subject is a mammal.

15. The method of claim 14, wherein the subject is a human.

16. The method of claim 14, wherein the VCP or fragment thereof is administered prior to or during reperfusion of a coronary artery.

17. The method of claim 13, wherein the VCP or fragment thereof is administered as a single bolus treatment.

* * * * *